United States Patent
Ruan et al.

(10) Patent No.: US 10,596,152 B2
(45) Date of Patent: Mar. 24, 2020

(54) SELENIUM CONTAINING KGA/GDH DUAL INHIBITORS AND THE APPLICATIONS THEREOF

(71) Applicant: HANGZHOU GAMMA BIOTECH CO., LTD., Hangzhou (CN)

(72) Inventors: Benfang Helen Ruan, Hangzhou (CN); Jennifer Jin Ruan, Hangzhou (CN)

(73) Assignee: HANGZHOU GAMMA BIOTECH CO., LTD., Hangzhou (CN)

( * ) Notice: Subject to any disclaimer, the term of this patent is extended or adjusted under 35 U.S.C. 154(b) by 0 days.

(21) Appl. No.: 15/983,079

(22) Filed: May 17, 2018

(65) Prior Publication Data

US 2018/0263961 A1   Sep. 20, 2018

Related U.S. Application Data

(63) Continuation-in-part of application No. PCT/CN2016/106202, filed on Nov. 17, 2016.

(30) Foreign Application Priority Data

Nov. 17, 2015 (CN) .......................... 2015 1 0789110

(51) Int. Cl.
   *A61K 31/41* (2006.01)
   *A61K 31/433* (2006.01)
   *A61K 31/454* (2006.01)
   *A61K 31/497* (2006.01)
   *A61K 33/04* (2006.01)

(52) U.S. Cl.
   CPC ............. *A61K 31/41* (2013.01); *A61K 31/433* (2013.01); *A61K 31/454* (2013.01); *A61K 31/497* (2013.01); *A61K 33/04* (2013.01)

(58) Field of Classification Search
   CPC .... A61K 31/433; A61K 31/545; A61K 31/41; A61K 31/497
   See application file for complete search history.

(56) References Cited

FOREIGN PATENT DOCUMENTS

CN         102234254    * 11/2011

OTHER PUBLICATIONS

Bioorganic & Medicinal Chemistry Ltters, 2013, vol. 23, No. 24, pp. 6737-6742(cited in the search report).*

* cited by examiner

*Primary Examiner* — Alexander R Pagano
*Assistant Examiner* — Ebenezer O Sackey
(74) *Attorney, Agent, or Firm* — Ladas & Parry, LLP (57) ABSTRACT

The present invention relates to the field of biomedicine, and discloses a class of selenium-containing inhibitors that bind to the allosteric site of glutaminase, and/or inhibit glutamate dehydrogenase, which has a long carbon chain or similar derivative structure linked with the N atom of benzoisoselenazole 3-ketone. The advantages of this invention are that compounds have novel binding activity with glutaminase and potent inhibitory activity of glutaminase. Moreover, some novel dual KGA/GDH inhibitors demonstrated good in vivo efficacy in inhibiting the tumor growth in mice by blocking glutaminolysis. At the meantime, compounds of this invention play an important part in the protection of survival, growth and differentiation of nerve cells under the condition of hypoxia-ischemia.

1 Claim, 2 Drawing Sheets

SELENIUM CONTAINING KGA/GDH DUAL INHIBITORS AND THE APPLICATIONS THEREOF

CROSS-REFERENCE TO RELATED APPLICATIONS

This application is a Continuation-In-Part application of PCT application No. PCT/CN2016/106202 filed on Nov. 17, 2016, which claims priority to Chinese application No. 201510789110.5, filed on Nov. 17, 2015, entitled "a selenium-containing KGA/GAC and/or inhibitory GDH compounds", the disclosure of which are hereby incorporated herein by reference in their entireties.

FILED OF THE INVENTION

The present invention relates to the field of biomedicine, and in particular to A composition of selenium-containing inhibitors that bind to the allosteric site of glutaminase and/or inhibit glutamate dehydrogenase, and also to the application of these compounds as a antitumor inhibitor in the treatment of urological cancer and also as a neuroprotective agent in the treatment of ischemic stroke.

BACKGROUND OF THE INVENTION

Gene mutations caused the so-called Warburg effect which showed dramatic changes in the aerobic glucose metabolic pathways in tumor cells. Specifically, glucose metabolism in tumor cells increases 200-fold over normal cells, but the lactic acid is excreted and cannot enter the mitochondrial tricarboxylic acid cycle of tumor cells. Hence glutamine becomes the necessary raw material for the production of energy in mitochondria of tumor cells, and meanwhile glutaminase is the essential enzyme assisting glutamine to be metabolized and fed into the mitochondrial tricarboxylic acid cycle. Therefore, any compound that causes the inhibition of glutamine metabolism or glutaminase activity, can inhibit the growth of tumor cells. On the other hand, elemental selenium also has an inhibitory effect on the growth of tumors, and the selenium in the human body produces different anticancer effects through a variety of metabolic mechanisms.

Ebselen (2-phenylbenzoisoselenazol-3-one) which is the best inhibitor for glutathione peroxidase (GPx), has been reported to also inhibit other enzymes, thus it is suspected to inhibit a variety of enzymes by selenium redox reactions, hence it lacks specificity and has low cellular activity.

For example, Ebselen was reported as a glutaminase inhibitor (IC50 9 nM) and a preferred inhibitor of glutathione peroxidase (GPx), but it is not potent in inhibiting glutamine dependent cancer cell growth (IC50, 20 uM).

Figure 1:
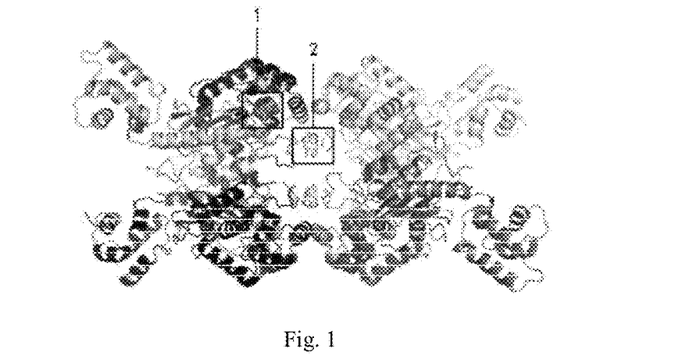
FIG. 1 shows the binding of GAC tetramer with BPTES.

We suspected that ebselen may not inhibit glutaminase. Therefore, we did biomolecular interaction analysis using ForteBio instrumentation, and discovered that ebselen was not good at binding glutaminase and 10 μM ebselen cannot directly combine toglutaminase. Therefore, based on the crystal structure of the allosteric site of glutaminase, we synthesized a series of new symmetric and asymmetric ebselen derivatives with the aim to make an ebselen derived KGA inhibitor. In the derivatives, the benzene ring at the 2-position of the original ebselen molecule was replaced by a straight-chain or branched alkyl substituent containing at least one carbon atom, or a long chain containing thioether, or a smaller cycloalkyl group, and the newly obtained derivatives are effective in binding to the allosteric site of glutaminase. The experiment showed that these compounds can directly bind to glutaminase, and their inhibitory activity to the growth of tumor cells (T24) increased 100-fold over ebselen. Moreover, these inhibitors that bind the allosteric site of glutaminase had good selectivity and higher potency for inhibition of tumor cell growth (<100 nM), and no damage to normal cells (10 μM). These inhibitors also had significant activity in an immunodeficient mouse model with no toxicity. These inhibitors had good inhibitory activity for various types of glutamine-dependent cancer cells (80-90%), especially urinary system tumors. The binding diagram of GAC tetramers and BPTES is shown in FIG. 1, wherein "mark 1" is the active site of substrate binding; and "mark 2" is an allosteric site for BPTES binding.

In addition, we added electro-withdrawing or electro-donating groups to the benzene ring of ebselen to increase or decrease the redox activity of compounds, optimize the pharmacological properties of compounds, the binding capacity with glutaminase, as well as the antitumor activity of compounds. The metabolism of glutamine (Gln) by glutaminase provides important material for the rapid synthesis of protein/lipid/nucleic acid in tumor cells and maintains the redox state. The growth of many tumor cells depend on glutamine, because it was fed into the mitochondrial tricarboxylic acid cycle, which makes; consequently, inhibitors of glutamine are predicted to inhibit the growth of tumors.

The invention found new drugs with high efficacy against cancer cells with low systemic toxicity. Since the growth of many tumor cells is dependent on the metabolism of glutamine in mitochondria, the inhibitors of glutaminase can inhibit the growth of tumors with little toxicity to normal cells. In the meantime, the molecular structure of ebselen was modified by replacing the benzene ring at the 2-position, with carbochains, carbocycles or derivatives thereof containing several carbon atoms, such as thioethers, or other derivatives including N, or O. These modifications are beneficial for compounds to bind with the allosteric site of glutaminase, meanwhile adding the electron-withdrawing group or electron-donating groups to the benzene ring of the selen moiety can increase or decrease the redox activity of compounds, and optimize the pharmacological properties of compounds, the binding capacity with glutaminase, as well as the antitumor activity of compounds. The synthesized compounds have the ability of targeting, inhibiting mitochondrial function and blocking the energy metabolism of tumors, in addition, they showed 100 folds better inhibition of glutaminase than that of ebselen, and have a very notable competence to inhibit glutamine-dependent tumor, which can be used for the treatment of tumors of urinary system or for the post-operative cancer prophylaxis.

In additional, glutamic acid is an important neural transmitter. Overloading glutamic acid is characteristic right after the onset of ischemic stroke, therefore glutaminase inhibitor might correct the overloading and protect the injured nerve cells from death. These compounds show clear evidence of cell protection under OGD condition (oxygen glucose deficient condition) which is an in vitro mimic of hypoxia-ischemia situation.

SUMMARY OF THE INVENTION

The objective of this invention is to provide a class of selenium-containing inhibitors that bind to the allosteric site of glutaminase, and/or inhibit glutamate dehydrogenase, and these compounds have the structural formula as shown below:

Or:

Or:

Or:

Or:

Or:

Wherein:

$R_1$, $R_2$, $R_3$, $R_4$, $R_5$, $R_6$, $R_7$, $R_8$ are independently selected substituents comprising H, C, N, O, S, Se, a linear or branched alkyl group in which at least one C is independently replaced by O, N or S, aromatic heterocycle, heterocycle, aromatic group, cycle group, substituted alkyl, lipid, or through amide, ether, halogen, silane, thioether, cynide, —NO$_2$, amine, acid, amine, phosphate group, sulfoxide and related derivatives thereof, R9, R10 are independently selected substituents comprising W1 as following formula:

wherein:

$X_2$ is independently selected from H, C, N, O, S, Se, a linear or branched alkyl group in which at least one C is independently replaced by O, N or S, aromatic heterocycle, heterocycle, aromatic group, cycle group, substituted alkyl, lipid, or through amide, ether, halogen, silane, thioether, cynide, —NO$_2$, amine, acid, amine, phosphate group, sulfoxide and related derivatives thereof, R11 is independently selected from H, or a linear or branched alkyl group in which at least one C is independently replaced by O, N or S, R12 is independently selected substituent comprising amine, cynide, alkyne, azide, amide, ether, halogen, silane, thioether, amine, phosphate group, sulfoxide, one or more cyclic, heterocyclic, aromatic, heteroaromatic groups, R13 is independently selected substituents comprising halides, alkyloxy group or X$_2$;

R7 is independently selected from biological active compounds, wherein:

heterocyclic is substituent comprising one or more fused cyclic rings in which at least one C is independently replaced by N, S, O or Se, Heteroaromatic group is substituent comprising one or more fused aromatic rings in which at least one C is independently replaced by N, S, O or Se.

$R_1$, $R_2$, $R_3$ and $R_4$ are not H atom simultaneously, and $R_5$, $R_6$, $R_7$ and $R_8$ are not H atoms simultaneously, or $R_1$, $R_2$, $R_3$, $R_4$, $R_5$, $R_6$, $R_7$, $R_8$ are H.

$R_1$, $R_2$, $R_3$, $R_4$, $R_5$, $R_6$, $R_7$ and $R_8$ are independent substituents selected from the group of aromatic heterocycle, substituted alkyl, amide, ether, lipid, halogen, silane, thioether, amine, phosphate group, sulfoxide, and sulfonyl.

When $R_9$ is a hydrogen atom, and $R_{10}$ is a substituent comprising 1 to 20 atoms selected from the group of C, H, N, O, S, P, Si and halogen atoms. Especially, $R_{10}$ is a substituent selected from the group consisting of aromatic heterocycle, substituted alkyl, amide, ether, lipid, halogen, silane, thioether, amine, phosphate group, sulfoxide, sulfonyl and related derivatives thereof.

Further, the present invention also exemplifies various compounds with the similar structure, for example:

Wherein:

R, $R_1$, $R_2$ are independently selected substituents comprising aromatic heterocycle, heterocycle, substituted alkyl, lipid, or through amide, ether, halogen, silane, thioether, amine, phosphate group, sulfoxide. R3 is H— or similar to R, $R_1$, $R_2$;

As a conventional knowledge, BOC is referred to as t-Butyloxy carbonyl in this application.

This invention also provides pharmaceutical compositions or mixtures of pharmaceutically active salts of the above-mentioned compounds. These pharmaceutical compositions or mixtures have other auxiliary ingredients in addition to the above-described active salt.

This invention also provides the efficacy of mentioned pharmaceutical compositions or mixtures in the treatment of cancers which are dependent on glutamine metabolism, the cancers contain the group of lung cancer, bladder cancer, prostate cancer, skin cancer and so on.

This invention also provides the efficacy of mentioned pharmaceutical compositions or mixtures in the protection of injured nerve cells caused by overloading glutamic acid or hypoxia-ischemia.

And a composition of selenium-containing inhibitors that bind to the allosteric site of glutaminase and/or inhibit glutamate dehydrogenase comprising a general formula as follows:

wherein:

$X_2$ comprising a linear or branched carbon chain containing 4-7 C, Hydroxylpyperidine, Pyrrolidine, Aminopyperidine, m-phenyldiamine or 3-7 membered cycle group, $R_4$, $R_5$ are independently selected substituents comprising H, C, N, O, S, Se atom, aromatic heterocycle, heterocycle, aromatic group, cycle group, substituted alkyl, lipid, or through amide, ether, halogen, silane, thioether, amine, phosphate group, sulfoxide, or related derivatives thereof.

wherein one or more C in linear or branched carbon chain are independently replaced by N, O, S or Se.

The application of the selenium-containing inhibitors that bind to the allosteric site of glutaminase and/or inhibit glutamate dehydrogenase according to claims 12, in combination with paclitaxel, 5-FU, kinase inhibitors and their analogs.

The application of the selenium-containing inhibitors that bind to the allosteric site of glutaminase and/or inhibit glutamate dehydrogenase according to claims 1, for having efficacy in the treatment of cancers which are dependent on glutamine metabolism and/or in the protection of injured nerve cells caused by overloading glutamic acid or hypoxia-ischemia, in combination with other therapeutic medicine.

Further modification or replacement of the selen motif to other aromatic rings, or replacement of the middle 6 carbon chains with heterocyclic group greatly improved the efficacy of the molecules.

Heterocyclic substituent is a heterocyclic functional group or substituent containing one or more heteroatoms independently selected from N, S, O, Se;

The polycyclic heteroaryl is a functional group or substituent fused by heterocyclic substituent and/or monocyclic aryl.

The similarities to the foregoing compounds are that they each have a long chain consisting of carbon atoms and may also include heteroatoms such as N, S, O, etc. Alternatively, the long chain can be replaced by a smaller ring, for example, a 2 to 4 membered ring, thereby the binding capacity of compounds with glutaminase can be increased, and the inhibitory effect on glutaminase is better. The length of the long chain can be arbitrarily varied, for example, $C_2$ carbon chain, $C_3$ carbon chain, $C_4$ carbon chain, $C_5$ carbon chain, $C_6$ carbon chain, $C_7$ carbon chain, $C_8$ carbon chain or longer chain containing more carbon atoms and their derivatives. The possible chain can be ethers, thioether, etc., which contains O, S, N elements whose position in the long chain can be arbitrarily changed. The long chain can also be replaced by cycloalkyl groups containing fewer carbon atoms, such as 3 to 5 carbon atoms, likewise, derivatives thereof are allowed.

Similarly, this invention also provides pharmaceutically active salts of the above-mentioned compounds and their pharmaceutical compositions or mixtures.

Compounds provided by this invention have a strong binding affinity for the allosteric site of glutaminase, can inhibit the activity of glutaminase effectively, and well inhibit tumor cells which are dependent on the glutamine to provide energy. Therefore, these compounds can be used for the treatment of urinary system tumors, as well as lung cancer and skin cancer, or for the post-operative prophylaxis.

BRIEF DESCRIPTION OF DRAWINGS

The invention is accompanied by six Drawings, wherein.

EXAMPLES

The present invention will be further described with the following examples. The terms used in this invention have general meaning as followed (unless otherwise specification).

The term "halogen" refers to halogen substituent from the group including fluoro (—F), chloro (—Cl), bromo (—Br), or iodo (—I); The term "halogenation" describes the above halogen substituent substitutes hydrogen of compound.

The term "alkyl" refers to straight-/branched-chain and cyclic saturated aliphatic hydrocarbon groups. It includes groups with single-ended bonds such as methyl, ethyl, propyl, isopropyl, butyl, primary/secondary/tertiary butyl, cyclopropyl, methylcyclopropyl, cyclobutyl; as well as alkyl groups with two or more free bonds but still meeting the valence-bond theory, such as —$CH_2$—, —$(CH_2)_2$—, —$(CH_2)_3$—, —$(CH_2)_4$—, —$C(CH_3)(CH_2)_2$—.

The term "substitute" describes the hydrogen atom of group is replaced by other functional group or substituent.

The term "aryl" refers to a functional group or substituent derived from simple aromatic ring; under the absence of other specification, it may either be a carbocyclic aryl group or heterocyclic aryl group containing heteroatom but not limited to N, S, O, etc.; besides, the aryl group may be a single ring or fused ring aryl; as well as a polycyclic substituent fused by aryl ring group with non-aryl ring.

The term "heteroaryl" refers to a functional group or substituent derived from an aromatic ring containing heteroatoms of different number of N, S, O, or other atoms.

The term "polycyclic heteroaryl" can refers to a heterocyclic aryl including but not limited to N, S, O atoms; as well as a fused ring aryl or a polycyclic substituent fused by aryl ring group with non-aryl ring.

Biological active substituents are any compounds or functional groups that have biological effect, and addition of the compound/ group could significantly improve the biological activity of the new molecules.

Example 1: Synthesis of Selen

After added 1,6-iaminohexane or other corresponding diamine compounds in a 50 mL flask, we added methylene chloride and TEA in the flask, and then added solution of 2-(chlorocarbonyl)-3-methylphenyl hypochloroselenoite, or other 2-chlorocarbonyl phenyl hypochloroselenoite substituted by benzene, in methylene chloride under stir and ice-cooling. After the addition, the ice bath was removed and the mixture was stirred overnight.

Post-treatment: To the white solid obtained by suction filtration, we added water and methanol. The mixture was stirred for 1 hour. The crude product was filtered and dried in dryer (50° C.).

The following product was obtained:
1. Hexane-(3,3'-dimethyl) selen

MS(ESI):529,100%:M+Na, LC:XDB-C18 4.6 mm×5 μm, methanol: water=60:40, V=1 mL/min, λ=254 nm;

1H NMR (500 MHz, DMSO) δ 7.80 (dd, J=7.7, 0.8 Hz, 1H), 7.63-7.57 (m, 1H), 7.45-7.39 (m, 1H), 3.71 (t, J=7.1 Hz, 2H), 2.5(s, 3H), 1.70-1.57 (m, 2H), 1.35 (t, J=6.8 Hz, 2H).

The following compounds were obtained by appropriately changing the substrate:
2. Hexane-(2,2'-difluoro) selen MS(ESI):537,100%:M+Na; LC:XDB-C18 4.6 mm×5 μm, methanol: water=60:40, V=1 mL/min, λ=254 nm; 1H NMR (500 MHz, DMSO) δ 7.80 (dd, J=7.7, 0.8 Hz, 1H),7.63-7.57 (m, 1H), 7.45-7.39 (m, 1H), 3.71 (t, J=7.1 Hz, 2H), 101.70-1.57 (m, 2H), 1.35 (t, J=6.8 Hz, 2H).

Example 2: Synthesis of Asymmetric Selen

To solid of 1,6-diaminohexane protected by BOC or other corresponding diamine compounds protected by BOC in a 50 mL flask, we added methylene chloride and TEA, and then added solution of 2-(chlorocarbonyl)-phenyl hypochloroselenoite—or other 2-chlorocarbonyl phenyl hypochloroselenoite substituted by benzene—in methylene chloride under stir and ice-cooling. After the addition, the ice bath was removed and the mixture was stirred overnight. A white solid was obtained by suction filtration and was then purified. The final product was:

3. Hexane-(2'-fluoro) selen

MS(ESI):519.3,100%:M+Na; LC:XDB-C18 4.6 mm×5 μm methanol: water=60:40, V=1 mL 20/min, λ=254 nm; m.p. 205.4~206.9° C.; 1H NMR (500 MHz, DMSO) δ 8.04 (d, J=8.0 Hz, 1H), 7.80 (dd, J=7.7, 0.8 Hz, 2H), 7.63-7.57 (m, 2H), 7.45-7.39 (m, 2H), 3.71 (t, J=7.1 Hz, 4H), 1.70-1.57 (m, 4H), 1.35(t, J=6.8 Hz, 4H).

The following compounds were obtained by appropriately changing the substrate:

4. N-{5-[5-[3-Oxo-3H-benzo[d]isoselenazol-2-yl)-pentyl]-[1,3,4]thiadiazol-2-yl}-2-phenyl-acetamide

MS(ESI):487.3,100%:M+H; 1H NMR (400 MHz, CDCl3) δ 7.99 (d, J=7.7 Hz,1H), 7.60-7.50 (m, 2H), 7.40 (dd, J=13.7, 7.4 Hz, 3H), 7.29-7.23(m, 4H), 4.02 (s, 2H), 3.82 (t, J=6.9 Hz, 2H), 3.01 (t, J=7.3 Hz,2H), 1.89-1.81 (m, 2H), 1.78-1.70 (m, 2H), 1.50 (dd, J=14.8, 7.6 Hz, 2H).

5. Phenyl-acetamido-[1,3,4]-thiadiazole-pentyl-[3'-methyl]-selenium

MS(ESI):504,100%:M+H; 1H NMR (400 MHz, CDCl3) δ 7.60-7.50 (m, 2H), 7.40(dd, J=13.7, 7.4 Hz, 3H), 7.29-7.23 (m, 4H), 4.02 (s, 2H), 3.82 (t, J=6.9 Hz, 2H), 3.01 (t, J=7.3 Hz, 2H), 1.89-1.81 (m, 2H), 1.78-1.70 (m, 2H), 1.50 (dd, J=14.8, 7.6 Hz, 2H).

6. Thioether selen

MS(ESI):533.3,100%:M+Na; LC:XDB-C18 4.6 mm×5 μm, methanol: water=60:40, V=1 mL/min, λ=254 nm; m.p. 205.4~206.9° C.; 1H NMR (500 MHz, DMSO) δ 8.04 (d, J=8.0 Hz, 1H), 7.80 (dd, J=7.7, 0.8 Hz, 1H), 7.63-7.57 (m, 1H), 7.45-7.39 (m, 1H), 3.71 (t, J=7.1 Hz, 2H) , 2.77 (t, J=6.8 Hz, 2H), 1.70-1.57 (m, 2H).

7. Thioethyletherselen

MS(ESI):485.0,100%:M+Na

8. Hexane-(N,N-dimethylamine-ethyloxyl)-hydroxyl-selen

MS(ESI):584.0:M+H;

9. Hexane-(N,N-dimethylamine-propyloxyl)-methoxyl-selen

MS(ESI):612.0:M+H;

12. N,N-dimethylethyloxy hexane selen

MS(ESI):652.0:M+H;

13. m-dimethyl benzene selen

MS(ESI):501.0:M+H;

14. m-dimethyl benzene N,N-dimethylethyloxyselen

MS(ESI):618.0:M+H;
17. Aminopyperidine-dithioazole-methoxyselen

MS(ESI):723.0:M+H;
18. Hydroxylpyperidine-dithioazole-methoxyselen

MS(ESI):724.0:M+H;
19. Pyrrolidine dithioazolemethoxy-selen

MS(ESI):739.0:M+H;

20. Aminopyperidine-dithioazolemethoxy-selen

MS(ESI):663.0:M+H;

21. Hydroxylpyperidine-dithioazole-selen

MS(ESI):664.0:M+H;

22. Pyrrolidine dithiodiazole-selen

MS(ESI):664.0:M+H;

23. m-phenyldiaminedithiodiazoleselen

MS(ESI):699.0:M+H;

24. cynide hexylselen

MS(ESI):594.0:M+H;

25. Alkyne hexylselen

MS(ESI):592.0:M+H;

26. biotin hexylselen

MS(ESI):849.1:M+H;
28. Pyridazine thiodiazoleSelen

MS(ESI):635.0:M+H;
29. Pyridazine thiodiazole Selen

Figure 2:
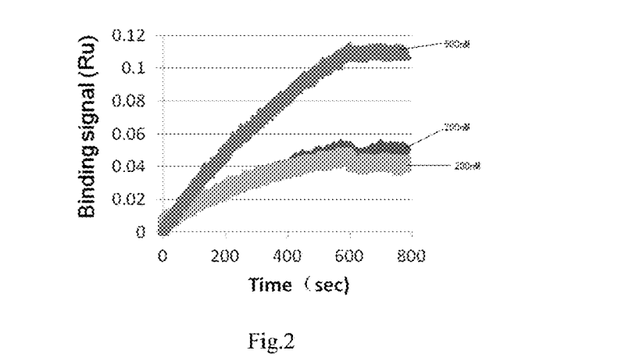
FIG. 2 shows the binding of synthetic thioether selen to glutaminase (KGA) by molecular interaction apparatus.

MS(ESI):624.0:M+H;

Example 3: The Binding of the Synthesized Compounds with Glutaminase by Molecular Interaction Apparatus As shown in FIG. 2, the KGA enzyme was immobilized on a ForteBio chip and was injected with solution of compound (0-1000 nM). The binding of the compound with enzyme was observed that different concentrations of hexane-(3,3'-methyl) selenium had distinct levels of combination with KGA enzyme, which was obvious.

Figure 3:
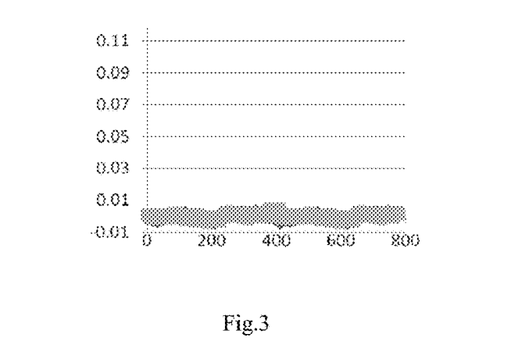
FIG. 3 shows the binding of the thioether selen to glutaminase by molecular interaction apparatus.

As shown in FIG. 3, ebselen (500 nM, 1000 nM) was not bound to the KGA immobilized on the chip. Many selen containing molecules, such as ebselen, ethylselen, propyl selen, tetraselen, were reported as strong inhibitors of TrxR, but we found that these selen compounds do not inhibit KGA, and is toxic to the normal cells. Whereas hexane selen and thioethylselen inhibit KGA, and is not toxic to the normal cells. Our Papers published are Anal. Chem. 2017, 89: 1689, ACS Chemical Biology, 2017, 12:3003

Example 4: Inhibition of Growth of Tumor Cells

Figure 4:
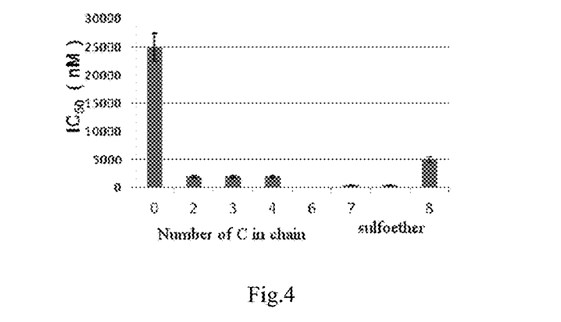
FIG. 4 shows the tumor cell viability after treatment with the compounds. Tumor cells (1000 cells per well) which were first treated with the corresponding compound for 3 days, and then EZMTT detection reagents were added measure the cell growth.

As shown in FIG. 4, compounds with different lengths of intermediate chain were added to tumor cells (1000 cells per well) culture, and the cell activity was detected by adding WST8 into cells after 3 days:

Wherein:

R represents 0 carbon atom, 2 carbon atoms, 4 carbon atoms, 6 carbon atoms, 7 carbon atoms (even thioether with 7 carbon atoms), or 8 carbon atoms.

The intermediate chain with 6 atoms (6 carbon or carbon chain containing a sulfur atom) has the best effect on cell viability (IC50 100-200 nM)

The results of the comparison of the activity of the new compound with the parent nucleus are shown below:

| Cells | Ebselen (Known compound) IC$_{50}$nM | Hexane- (2,2'-difluoro) selen (new compound) IC$_{50}$nM | Hexane- (3,3'-dimethyl) selen (new compound) IC$_{50}$nM | Thioether selen (new compound) IC$_{50}$nM |
|---|---|---|---|---|
| A549 | >10000 | 500 | 500 | 500 |
| PC12 | >10000 | 5000 | 5000 | 5000 |
| T24 | >10000 | 10 | 200 | 500 |
| PC3 | >10000 | 2000 | 2000 | 2000 |
| JC82 | >10000 | 2000 | 5000 | 5000 |
| Caki | >10000 | 1000 | 1000 | 1000 |
| L2 (Normal) | >10000 | >10000 | >10000 | >10000 |

The following is the inhibitory effect of the new compounds on bladder cancer cell lines:

| Compounds | T24 (Bladder cancer) IC$_{50}$nM | L2 (Normal cell) IC$_{50}$nM | Protection of PC12 cells under OGD |
|---|---|---|---|
| Ebselen | >10000 | >10000 | 1000 nM |
| Hexane - (2'-fluoro) selen | 200 | >10000 | <100 nM |
| Hexane-selenaphtholine | 210 | >10000 | <100 nM |
| Alkyl-selenoquinoline | 150 | >10000 | <100 nM |
| Hexane - (perfluoro) selen | 180 | >10000 | <100 nM |
| Hexane - (3,2'-difluoro) selen | 230 | >10000 | <100 nM |
| Hexane - (1-methyl, 2'-fluoro) selen | 220 | >10000 | <100 nM |
| Hexane- (2-methyl, 2'-methoxy) selen | 200 | >10000 | <100 nM |
| Phenyl-acetamido-[1,3,4]-thiadiazole-pentyl-[3'-methyl]-selenium | 1000 | >10000 | <100 nM |
| Hexane-selen | 500 | >10000 | <100 nM |
| p-xylene selen | 2000 | >10000 | <100 nM |
| 1,6- tert butyl carbonate hexamethylendiamineselen | 10000 | >10000 | <100 nM |
| Compound 7-25, 28, 29 | 1-200 nM | | 5 nM |

Compound 7-28 are still KGA allosteric inhibitors showed improved solubility, potency, and stability. Compound 26 was successfully coupled with biotine, and this approach is useful in generate additional compounds by linking with other anticancer drugs to improve efficacy.

Example 5: Animal Model of Subcutaneous Tumor

Figure 5:
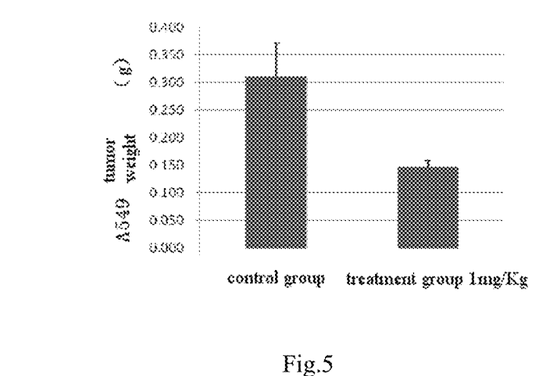
FIG. 5 shows the inhibition of the growth of the A549 tumor in immune deficient mice by thioether selen.

A549 tumor cells (1,000,000) were inoculated in nude mice, and the tumor size was 10 mm×10 mm in 24th to 27th day. Then compound hexane-(3,3'-dimethyl) thioether selen in PBS solution (200 μl) was injected subcutaneously every day near the tumor with the dosage of 1 mg/kg. The tumors (n=3) were resected after 7 days, and the results were shown in FIG. 5.

Figure 6:
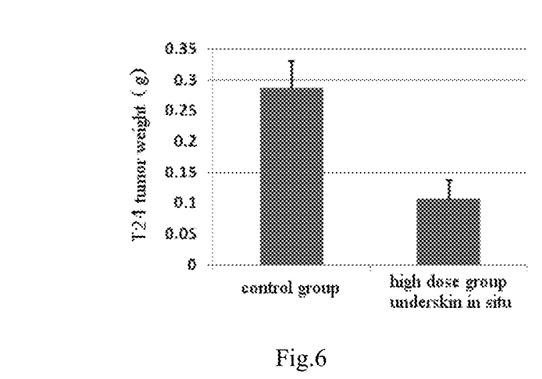
FIG. 6 shows the inhibition of the growth of the T24 tumor cells in immune deficient mice thioether selen

T24 tumor cells (1,000,000) were inoculated in nude mice, and the tumor size was 10 mm×10 mm in 24th to 27th day. Then compound hexane-(3,3'-dimethyl) thioether selen in PBS solution (200 μl) was injected subcutaneously every day near the tumor with the dosage of 1 mg/kg. The tumors (n=6) were resected after 7 days, and the results were shown in FIG. 6.

Figure 7:
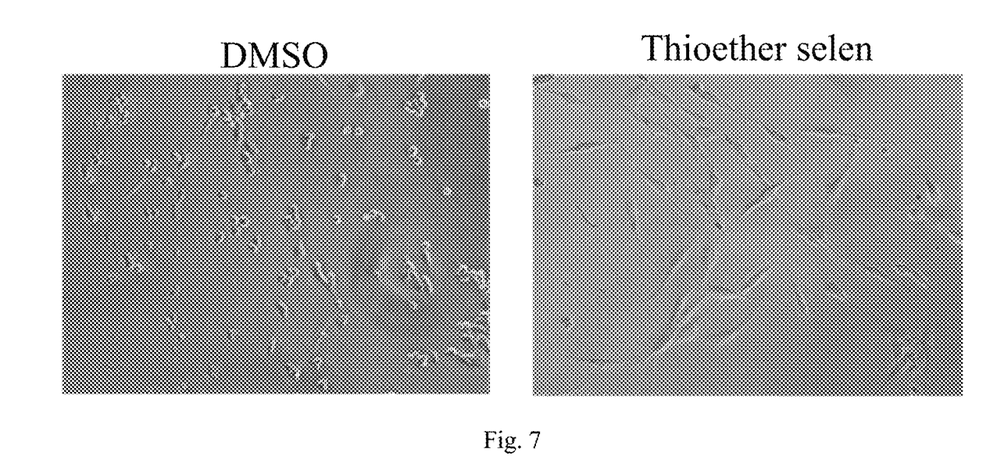
FIG. 7 shows the protection of PC12 neuronal cells under the OGD condition by thioether selen.

Compound 7-27 are still KGA allosteric inhibitors showed improved solubility, potency, and stability. In animal studies demonstrated better bioavailabilty and efficacy and low toxicity. Example 6: the growth experiment of protected nerve cell under the condition of hypoxia-ischemia As shown in FIG. 7, the compounds with different lengths of intermediate chain were added to the nerve cells (PC12; 1000 cells per well), and cells grew for 3-5 days under the condition of OGD hypoxia-ischemia. Then observed the growth of cellular neurite growth or neural synapse.

In conclusion, the foregoing examples are preferred embodiments of the present invention, it will be appreciated that modification can be made without departing from the spirit of the invention. Such modifications are intended to fall within the scope of the appended claims.

The invention claimed is:

1. A composition of selenium-containing inhibitors that bind to the allosteric site of glutaminase and/or inhibit glutamate dehydrogenase, selected from the following compounds:

23
-continued

24
-continued

31
-continued

32
-continued

Wherein:

R, $R_1$, $R_2$ are independently selected substituents comprising aromatic heterocycle, heterocycle, substituted alkyl, lipid, amide, ether, halogen, silane, thioether, amine, phosphate group, and sulfoxide.

* * * * *